United States Patent [19]

Jankewitz

[11] Patent Number: 4,622,985

[45] Date of Patent: Nov. 18, 1986

[54] APPLICATOR TIP AND COSMETIC APPLICATOR PROVIDED THEREWITH

[75] Inventor: Axel Jankewitz, Fürth-Oberfürberg, Fed. Rep. of Germany

[73] Assignee: A. W. Faber-Castell GmbH & Co., Nuremberg, Fed. Rep. of Germany

[21] Appl. No.: 589,666

[22] Filed: Mar. 14, 1984

Related U.S. Application Data

[63] Continuation-in-part of Ser. No. 304,045, Sep. 21, 1981, Pat. No. 4,452,262.

[51] Int. Cl.$^4$ .............................................. A45D 40/30
[52] U.S. Cl. .................................. 132/88.5; 132/88.7; 401/59; 401/198; 401/199
[58] Field of Search ................... 132/88.5, 88.7, 79 D; 401/198-199, 59

[56] References Cited

U.S. PATENT DOCUMENTS

| D. 255,367 | 5/1980 | Montague | D19/55 |
| 2,336,328 | 12/1943 | Whalen | 132/88.7 |
| 2,374,065 | 4/1945 | Worthington | 132/88.7 UX |
| 2,442,503 | 6/1948 | Melnikoff | 132/88.7 |
| 2,545,444 | 3/1951 | Braselton | 132/88.7 |
| 3,510,934 | 5/1970 | Koelichen | 401/198 X |

FOREIGN PATENT DOCUMENTS

| 1511388 | 7/1969 | Fed. Rep. of Germany . |
| 2621544 | 12/1976 | Fed. Rep. of Germany . |
| 1206239 | 8/1959 | France . |
| 1416928 | 9/1965 | France . |
| 1461650 | 11/1966 | France . |
| 279972 | 11/1964 | Netherlands | 401/199 |
| 407434 | 8/1966 | Switzerland . |

Primary Examiner—Gregory E. McNeill
Attorney, Agent, or Firm—Michael J. Striker

[57] ABSTRACT

An applicator tip has a substantially circular capillary body with a working end formed as a paraboloid with an inclined substantially flat cutting surface so as to form an applying surface to apply a solving medium areally, a curved applying edge to apply it over small areas, and a substantially pointed applying apex to apply a solving medium pointedly, as well as a cosmetic applicator provided with such applicator tip.

12 Claims, 6 Drawing Figures

FIG.1  FIG.2  FIG.3
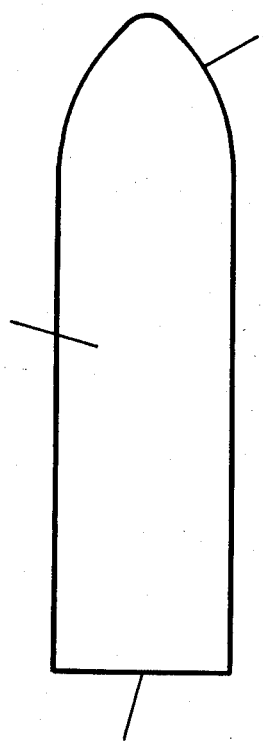
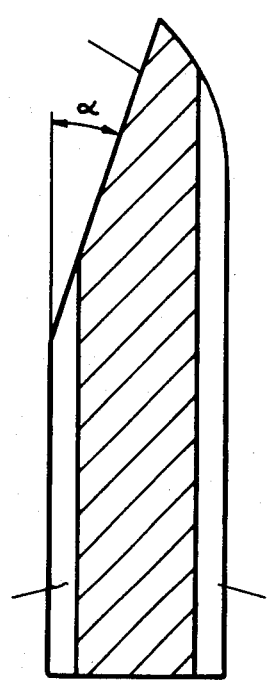
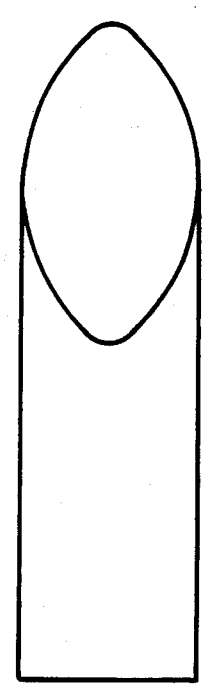
FIG.4
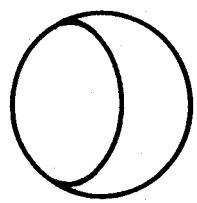

F I G. 6
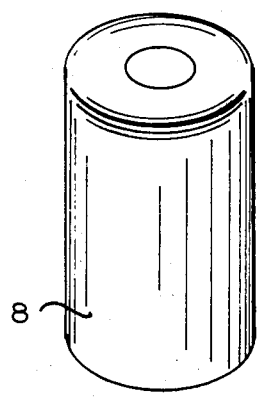
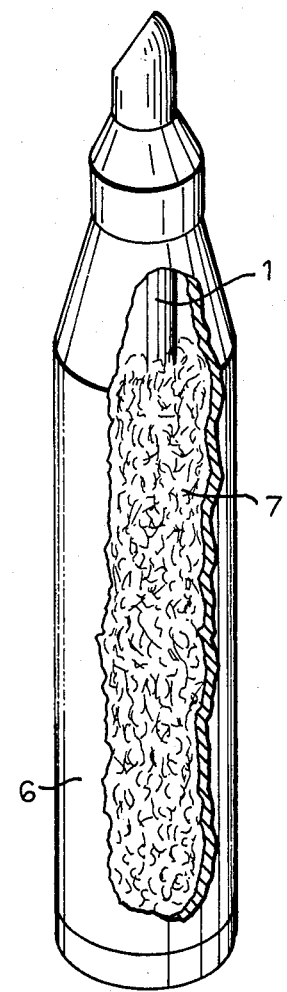

APPLICATOR TIP AND COSMETIC APPLICATOR PROVIDED THEREWITH

CROSS-REFERENCE TO RELATED APPLICATION

This application is continuation-in-part of application Ser. No. 304,045, filed Sept. 21, 1981, now U.S. Pat. No. 4,452,262.

BACKGROUND OF THE INVENTION

The present invention relates to an applicator tip and a cosmetic applicator provided therewith.

Cosmetic applicators are known in the art. A known cosmetic applicator includes a storage container and a capillary applicator tip which is impregnatable with a solving medium and extends outwardly beyond the storage container through an opening which is formed as a guide opening. A lead sealingly closes the storage container and is removable for use of the applicator. During application of coloring cosmetics, surfaces of skin, fingernails or toenails are often colored in undesirable manner. Especially when an inexperienced person applies coloring cosmetics, it is often required to release the colored skin or nail parts from previously applied cosmetics before a new cosmetic application. Wool pieces or cotton bars, or so-called Q-tips impregnated with a solving medium, are as a rule used for this purpose. However, they do not provide for the possibility to exactly remove the previously applied cosmetics.

German patent application P No. 3,202,435 discloses an applicator which is formed as a cosmetic cleaning device with a capillary tip, which is suitable for desired application of a solving medium. The capillary tip is formed as a fiber wick with a circular cross section and an end produced by an inclined cut. The known capillary tipes, for example formed as fiber wicks, have the property that during the production of the strand the radially outer zone in which the fibers are connected with one another by synthetic plastic adhesive is denser than the radially inner zone. This increased density leads to the fact that the radially outer zone possesses a high strength so as to provide a certain hold to the tip. However, this also possesses the disadvantage that, in the radially outer zone, almost no passage of the liquid to be applied takes place. As a result of this, at the inclined end of the tip, and particularly at its apex, only small quantities or no solving medium at all are available. This especially disadvantageous when the user turns the tip so that the denser outer zone lies on the skin.

SUMMARY OF THE INVENTION

Accordingly, it is an object of the present invention to provide an applicator tip and a cosmetic applicator which in a radially outer zone no longer have a reduced passage of liquid and allows a desired and areally limited application of liquids.

In keeping with these objects and with others which will become apparent hereinafter, one feature of the present invention resides, briefly stated, in an applicator tip which has a body of circular cross section and a working end formed as a paraboloid with an inclined, substantially flat cutting surface which forms an applying surface to apply a medium areally, a curved applying edge to apply a medium linearly, and a substantially pointed apex for applying a medium pointedly.

It is also another feature of the present invention to provide a cosmetic applicator with the applicator tip in accordance with the present invention.

By cutting a part of the paraboloid by a flat cutting surface, the remaining portion of the tip does not have a denser zone. The paraboloid shape of the working end of the tip is spaced from the unfavorable radially outward zone. The thus formed working end is composed exclusively of a radially inner part of the tip, in which the capillarity is available to a full extent.

In accordance with another advantageous feature of the present invention, the cutting surface is formed so that the user can maintain the natural holding Of the cosmetic applicator in the hand. This feature is that the angle of the cutting surface to the axis of the applicator tip lies in a region between 15° and 30°. When the applicator tip is designed in accordance with this feature, it is possible in the event of undesirable cosmetic application on the lower side of a nail, to penetrate with the working end of the tip into this region and dissolve and remove the cosmetic substance therefrom.

An especially good handling and visibility during guiding of the tip is obtained when the inclined cutting or section surface extends from an apex of the paraboloid to an outer surface of the body. This advantage is also maintained when the inclined cutting surface extends outwardly beyond the axis of the tip, but does not reach the denser radially outer zone or region at the opposite radial side of the tip.

The novel features which are considered characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

FIG. 1 is a side view showing a tip for cosmetic applicator from a rear side of a flat cutting surface;

FIG. 2 is a view showing a section of the applicator tip in accordance with the present invention;

FIG. 3 is a side view, as seen normal to the flat cutting surface of the inventive applicator tip;

FIG. 4 is a plan view of the tip in accordance with the present invention;

FIG. 6 is a schematic view showing a cosmetic applicator with the applicator tip of the present invention.

DESCRIPTION OF THE PREFERRED EMBODIMENTS

Figure 5:
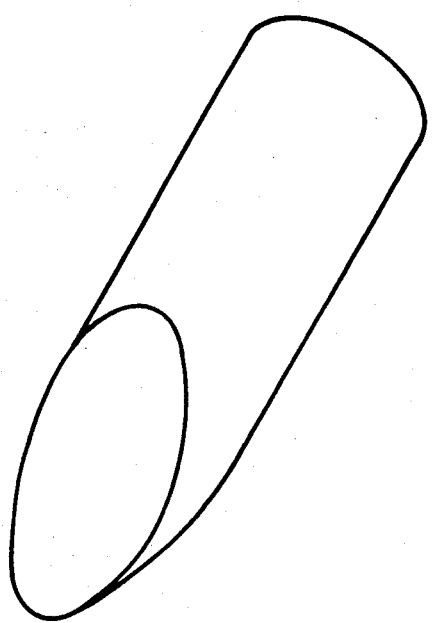
FIG. 5 is a perspective view of the tip according to the present invention with the inclined cutting surface.

An applicator tip for a cosmetic applicator is identified as a whole with reference numeral 1. It has a substantially circular cross section. The tip 1 has a dull end 2 to be held in a cosmetic applicator. A working end 3 which is opposite to the end 2 is formed as a paraboloid or, more particularly, as a part of a paraboloid. Then it is cut by an inclined cutting or sectioning surface as shown in FIG. 2. More particularly, the cutting surface extends from one radial side of the tip to the other radial side and does not end at the axis of the tip. Instead, the cutting surface, which is identified with reference numeral 4, extends outwardly beyond the axis of the tip.

The tip 1 is composed of a plurality of fibers extending in its axial direction and connected with one another by a synthetic plastic adhesive. The fibers can be composed of polyester whereas, the adhesive can be composed of epoxy resin. As can be seen from FIG. 2, a radially outer zone 5 of the tip 1 contains the fibers which are arranged denser than the fibers in the radially inner zone close to the axis of the tip. The cutting surface 4 extends, as mentioned above, radially outwardly beyond the axis of the tip, but ends in the radially inner zone shortly before the radially outer zone 5. Since the radially inner zone is less dense and is better for passage of a liquid medium, all parts of the working end of the tip are actually located in the region of the radially inner zone with improved passage properties.

The cutting surface 4 extends at an angle of between 15° and 30" to the axis of the tip.

When the applicator tip is designed in such a manner, it has a substantially ellipsoidal application surface corresponding to the cutting surface 4, a convexly curved application surface provided in the remaining region of the working end behind the cutting surface 4, and a substantially pointed application apex in the region of intersection of the cutting surface and the convexly curved surface.

For applying liquids, particularly a solving medium, the tip can be used in various ways. For obtaining a wide-surface application, the cutting surface 4 is applied completely onto a countersurface. For a small-surface application, the remaining convexly curved outer surface of the paraboloid 3 is brought into contact with a countersurface. For a pointed application of liquids, the outermost apex of the paraboloid 3 can be used.

As can be seen from FIG. 6, the applicator tip in accordance with the present invention can be used in a cosmetic applicator which has a storage container 6, a tampon 7 impregnated with a liquid such as a solving medium, and a lid 8 which sealingly closes the container over the working end of the tip 1. The tip 1 is in liquid-conducting communication with the tampon 7. Of course, the cosmetic applicator for the tip in accordance with the present invention can be formed in many other ways.

It will be understood that each of the elements described above, or two or more together, may also find a useful application in other types of constructions differing from the types described above. While the invention has been illustrated and embodied in an applicator tip and a cosmetic applicator provided therewith, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims;

1. An applicator tip for cosmetic applicator, comprising a body at least partially composed of a capillary material impregnatable with a liquid medium, said body having a substantially circular cross section with an axis, a working end for applying a medium and a holding end to be held, said working end being formed as a paraboloid intersected by an inclined substantially flat cutting surface so as to form a flat application surface for applying a liquid medium over wide surfaces, a convexly curved application surface for applying a liquid medium over small surfaces, and an application apex for applying a liquid medium pointedly.

2. An applicator tip as defined in claim 1, wherein said body has an outer surface, said cutting surface extending from said outer surface to said body toward said axis of said body.

3. An applicator tip as defined in claim 1, wherein said cutting surface of said body extends at an angle substantially between 15° and 30° to said axis of said body.

4. An applicator tip as defined in claim 1, wherein said body has an outer surface, said cutting surface extending from said pointed apex of said paraboloid to said outer surface of said body.

5. An applicator tip as defined in claim 1, wherein said body has an outer surface, said cutting surface extending from said outer surface at one radial side of said body toward the opposite radial side of said body and outwardly beyond said axis so as to stop short of the opposite radial side of said body.

6. An applicator tip as defined in claim 1, wherein said body is composed of a plurality of fibers extending substantially in an axial direction.

7. An applicator tip as defined in claim 6; and further comprising means for connecting said fibers with one another including a synthetic plastic adhesive.

8. An applicator tip as defined in claim 6, wherein said body has a radially inner region and a radially outer region, said fibers in the radially outer region being located denser than said fibers in said radially inner region of said body.

9. An applicator tip as defined in claim 5, wherein said body has a radially inner region and a radially outer region and is composed of a plurality of fibers extending in an axial direction and arranged so that said fibers in said radially outer region are located denser than said fibers in said radially inner region, said cutting surface ending outwardly beyond said axis of said body in said inner region of said body without reaching said outer region with denser fibers.

10. A cosmetic applicator for applying a solving medium, comprising a storage container bounding an inner chamber for containing a solving medium; a lid movable relative to said storage container between an open position and a closed position; and an applicator tip extending outwardly from said container and formed as defined in claim 1.

11. A cosmetic applicator as defined in claim 10; and further comprising a tampon insertable into said inner chamber of said storage container and impregnatable with a solving medium, said applicator tip being associated with said tampon so as to receive from said tampon the solving medium and apply it.

12. An applicator tip for cosmetic applicator, comprising a body at least partially composed of a capillary material impregnatable with a liquid medium, said body having a substantially circular cross section with an axis, a working end for applying a medium and a holding end to be held, said working end being formed as a paraboloid intersected by an inclined substantially flat cutting surface so as to form a flat application surface for applying a liquid medium over wide surfaces, a convexly curved application surface for applying a liquid medium over small surfaces, and an application apex for applying a liquid medium pointedly, said body having a radially inner region and a radially outer region, said radially inner region having a lower density, and said radially outer region having a higher density.

* * * * *